United States Patent [19]
Hollis

[11] Patent Number: 5,402,800
[45] Date of Patent: Apr. 4, 1995

[54] ANKLE LAXITY MEASUREMENT SYSTEM

[76] Inventor: J. Marcus Hollis, 5509 Scenic Dr., Little Rock, Ark. 72207

[21] Appl. No.: 100,859

[22] Filed: Aug. 2, 1993

[51] Int. Cl.⁶ .............................................. A61B 5/10
[52] U.S. Cl. ................................... 128/779; 128/782
[58] Field of Search ................. 128/774, 779, 782; 33/511, 512

[56] References Cited

U.S. PATENT DOCUMENTS

| | | |
|---|---|---|
| 4,062,355 | 12/1977 | Kaye . |
| 4,323,080 | 4/1982 | Melhart ........................ 128/782 |
| 4,437,473 | 3/1984 | Mollan . |
| 4,549,555 | 10/1985 | Fraser et al. . |
| 4,571,834 | 2/1986 | Fraser et al. . |
| 4,649,934 | 3/1987 | Fraser et al. . |
| 4,667,685 | 5/1987 | Fine . |
| 4,799,497 | 1/1989 | Riley et al. . |
| 4,804,000 | 2/1989 | Lamb et al. . |
| 4,823,807 | 4/1989 | Russell et al. . |
| 4,909,262 | 3/1990 | Halpern et al. . |
| 4,913,163 | 4/1990 | Roger et al. . |
| 5,012,820 | 5/1991 | Meyer ........................... 128/782 |
| 5,050,618 | 9/1991 | Larsen . |
| 5,078,152 | 1/1992 | Bond et al. . |
| 5,228,454 | 7/1993 | Siegler ......................... 128/782 |

FOREIGN PATENT DOCUMENTS

| | | | |
|---|---|---|---|
| 2641183 | 7/1990 | France ................... | 128/779 |
| 231711 | 11/1968 | U.S.S.R. . | |
| 0677747 | 8/1979 | U.S.S.R. ............... | 128/779 |

OTHER PUBLICATIONS

"In VIVO Measurement of Instability of the Ankle", Taga et al., ORS, 38th Annual Mtg., Feb. 17, 1992.
ISA Transactions, vol. 17, No. 1, p. 18 1978.

Primary Examiner—Max Hindenburg
Attorney, Agent, or Firm—Jim Zegeer

[57] ABSTRACT

An ankle laxity measurement system for measuring laxity of the ankle and subtalar joint of a patient, includes a foot clamp frame securable to the patient's foot. A reference point is established on the patient's tibia above the patient's ankle. Motion between said foot clamp frame and the reference point is measured in six degrees of freedom. A handle secured to the frame to apply a force which is measured in anterior-posterior and inversion-eversion directions. Signals corresponding to these forces and the six degree of freedom movements are supplied to a computer to compute, record and display the measured motions and loads.

12 Claims, 7 Drawing Sheets

ANKLE LAXITY MEASUREMENT SYSTEM

BACKGROUND OF THE INVENTION

The ankle joint in medicine is the joint between the tibia-fibula and the talus bones. In a more layman terminology the ankle also includes the joint between the talus and the calcaneus (the subtalar joint). A ligament injury to the ankle is the most common ligament injury and is one of the most common musculoskeletal injuries. Fortunately these injuries usually heal without long term problems. Sometimes, however, the ligaments do not heal in such a way to provide biomechanical stability to the ankle and this causes chronic instability of the ankle. This chronic instability and giving way of the ankle can lead to pain, reinjury and degeneration in the joint and arthritis. Several surgical procedures have been developed to repair the ligaments of the ankle with no clear consensus as to which one is the preferable.

The ligaments which are most commonly injured are on the lateral (outside) side of the foot and consist of the anterior talo-fibular ligament and the calcaneo-fibular ligament.

In order to diagnose an injury to the ligaments of the ankle a laxity test is performed on the ankle. Usually this is done by holding the tibia with one hand and the foot with the other hand. Then an anterior-posterior (forward and backward) or inversion-eversion (twisting inward and outward) load is applied to the foot and the resulting motion is observed. This technique is highly subjective and subject to error since it is difficult to distinguish between the motion with or without the injured ligaments.

PRIOR ART

In a paper by Taga et al., entitled "In Vivo Measurement Of Instability Of The Ankle", ORS, 38th Annual meeting, Feb. 17, 1992, a measurement device is disclosed which has a calf holder which slides free in a direction right to the tibial axis. The anterior-posterior load can then be applied manually to the tibia only and the load on the foot is detected by a strain-gauge type load cell built into the base of the foot fixing unit. Displacement transducers are placed in contact with the anterior aspect of the distal tibia and the posterior aspect of the calcaneus and relative displacement between them is displayed.

U.S. Pat. No. 4,913,163 relates to the measurement of laxity of the anterior cruiate ligament of the knee. It measures the movement of the tibial tuberosity of the patient's leg relative to the patella. A computer plots and displays the output on a monitor.

U.S. Pat. Nos. 4,571,834, 4,799,947, 4,549,555, 4,823,807, 4,649,934, 5,078,152 and 4,909,262 and, patent document T100602 disclose the measurement of laxity of the knee. Most of these references utilize some form of an electrical read-out.

ISA Transactions, Vol. 17, No. 1, discloses a technique of evaluating knee, hip and ankle which includes an apparatus shown on page 18, FIG. 12A.

The following references are of interest in that they disclose the measurement of the knee, leg and ankle movements and stress of the muscles: U.S. Pat. No. 4,062,355, 4,323,080, 4,804,000, 4,437,473, 5,050,618, 4,667,685, and Russian Patent Document No. 231711 which discloses recordings of wrist movements.

THE PRESENT INVENTION

In contrast to the above prior art, the present invention provides a method and apparatus for measuring ankle laxity in both the anterior-posterior direction and the inversion/eversion angulation and provides more precise and reproducible results than can be done by hand or any of the other devices disclosed above.

The present invention is capable of establishing the range motion laxity in normal subjects, and the amount of increase in motion which is usually seen in the ankle when a particular structure is injured. This information, when combined with a laxity test on a patient's ankle can help diagnose a ligament injury and also detect if there is an instability in the ankle once the ligament has healed. The invention can also be used to examine the results of ankle ligament surgery.

According to the invention, measuring of laxity of the ankle and subtular joint of a patient includes a foot clamp frame and means for securing the foot clamp frame to the patient's foot. A further unit establishes a reference point on the patient's tibia above the patient's ankle and includes means for securing the unit to the patient's lower leg. A foot clamp frame is secured to the patient's foot and includes means to measure motion between the foot clamp frame and the reference point in SIX degrees of freedom. Moreover, a handle is secured to the foot clamp frame and includes a force measuring device to measure the anterior-posterior and inversion-eversion forces applied through the handle to the foot clamp frame and a record and display of the measured motion and loads is made, preferably, by a digital computer. In a preferred embodiment the foot clamp frame includes a pad means positioned on the foot clamp frame on either side of the calcaneus and the pad means on the posterior of the calcaneus. A further pad bridges the top of the patient's foot and each is adjustable to produce a secure fit on the patient's foot. The foot clamp frame includes a base plate underneath the patient's foot and it has a series of holes which are selectable for adjusting the foot clamp frame to accommodate different patient's feet. The six degree of freedom mechanism can include a kinematic linkage or be fully electronic.

BRIEF DESCRIPTION OF THE DRAWINGS

The above and other objects, advantages and features of the invention will become more apparent when considered with the accompanying specification and attached drawings wherein.

DETAILED DESCRIPTION OF THE INVENTION

Figure 2:
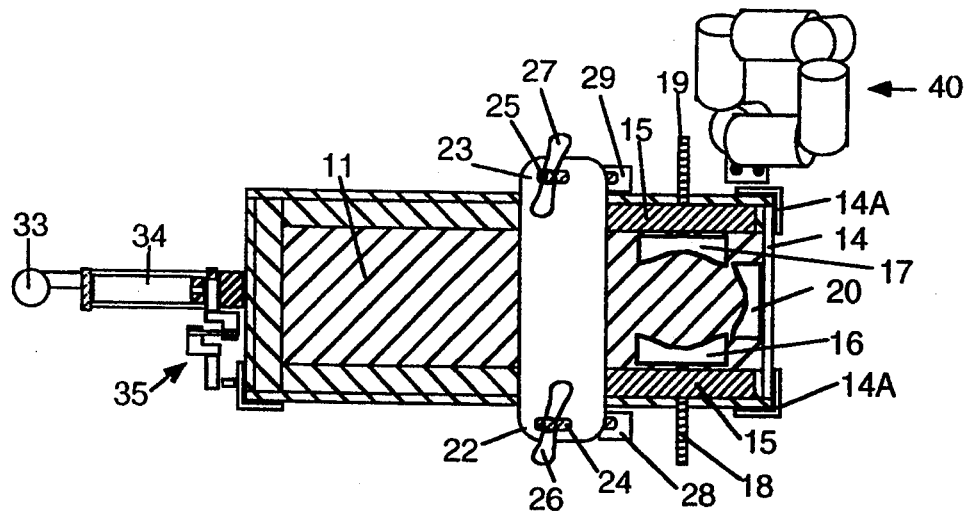
FIG. 2 is a top plan view thereof.
Figure 1:
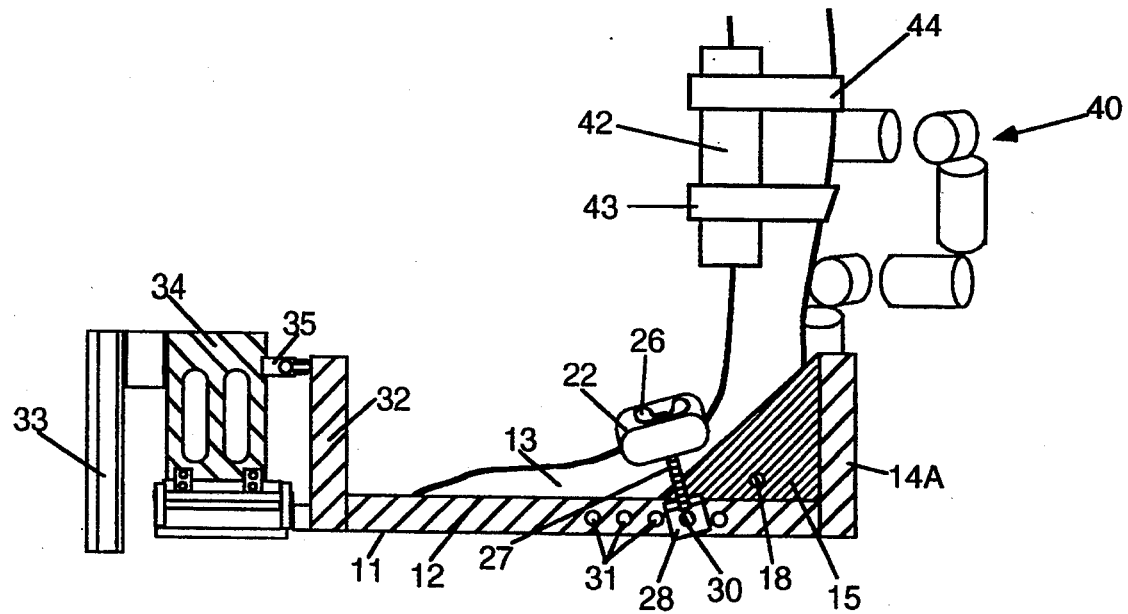
FIG. 1 is a side elevational view of a first embodiment of the invention.

Referring now to the embodiment shown in FIGS. 1 and 2, a foot clamp frame 10 is provided with a base plate 11 upon which the bottom 12 of the patient's foot 13 rests, a back plate 14 which is secured to base plate 11 by angle members 14A and side gusset plates 15. Calcaneus pads 16 and 17 engage the sides of the largest tarsal bone forming the prominence of the heel and are adjustable inwardly and outwardly on threaded rods 18 and 19, respectively, so as to accommodate different size patients. Pad 20, in conjunction with pads 18 and 19 and the adjustment thereof, snugly accommodate the patient's foot.

Foot pad 21 has lateral ends 22, 23 through which pass threaded adjustment rods 24, 25, respectively, which receive wing nuts 26, 27 so as to provide a further adjustment to accommodate the patient's foot. Moreover, the lower ends of threaded rods 24, 25 are provided with blocks 28, 29 which have a stud 30 received in one of a series of adjustment holes 31 formed in both sides of base plate 11 without in any way impeding movement of the ankle joint, which occurs in two planes. The toe end 32 of the foot clamp frame includes a load handle 33 which is coupled via an anterior-posterior load cell 34 to the toe end 32 and an inversion-eversion load cell 35. The anterior-posterior 34 and inversion-eversion 35 load cells can be of various types such as those manufactured by Omega Engineering and designated #LCL-040 and by Auntleight designated #1010-505H. Moreover, the types of load cells can be mixed in a given embodiment.

Figure 3:
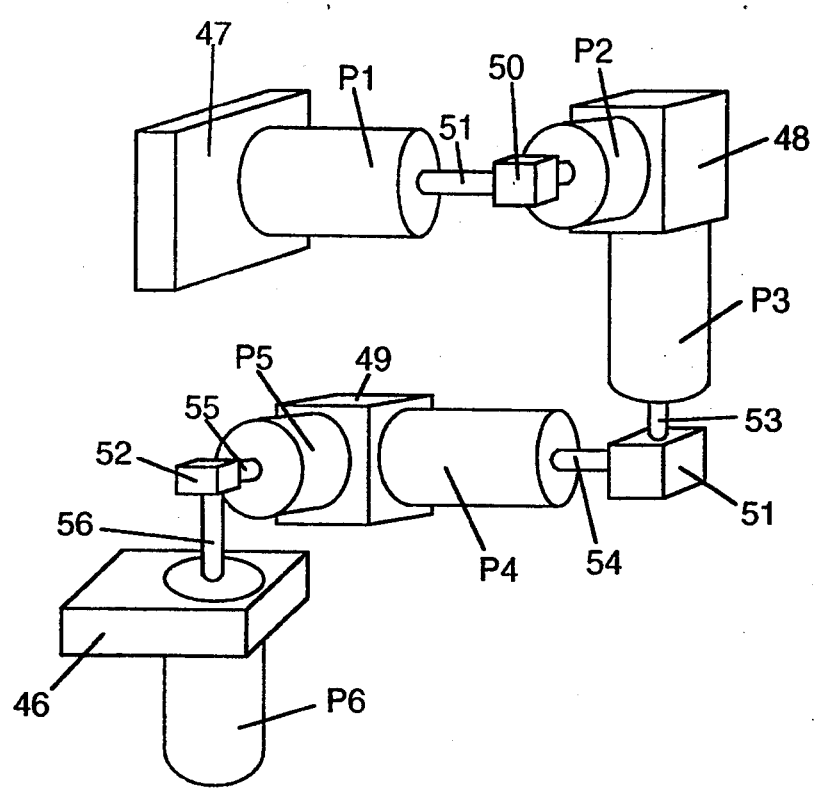
FIG. 3 is a view illustrating a linkage detail showing the potentiometer linkage for the 6 degrees of freedom measurement.

In the embodiment shown in FIGS. 1 and 2, a six degree of freedom spatial kinematic linkage 40 is provided, to monitor the motion of a calcaneus with respect to the tibia. A point of reference is established on the tibia by tibia pad 42 which is secured to the calf of the patient's leg by velcro straps or fasteners 43, 44. As shown in FIG. 3, the linkage includes six rotary potentiometers P1, P2, P3, P4, P5 and P6 with a bracket 46 securing the potentiometer P6 to the foot clamp frame 11 and mounting bracket 47 secures the other extremity of rotary potentiometers P1 to the tibia attachment pad 42. Each rotary potentiometer includes a shaft S1 which rotates relative to the potentiometer component in the main body. The intermediate potentiometers P2, P3 and intermediate potentiometers P4 and P5 have their potentiometer bodies secured by mounting frame members 48 and 49. The shafts of potentiometers P1 and P2 are secured together at right angles by members 50, the shaft S3 of potentiometer P3 and the shaft S4 of potentiometer P4 are likewise secured at right angles by member 51 and, the shafts of potentiometers P5 and P6 are secured at right angles by bracket member 52. This six degree of freedom spatial kinematic linkage 40 allows measurement of all motion of the calcaneus with respect to the tibia.

Figure 7:
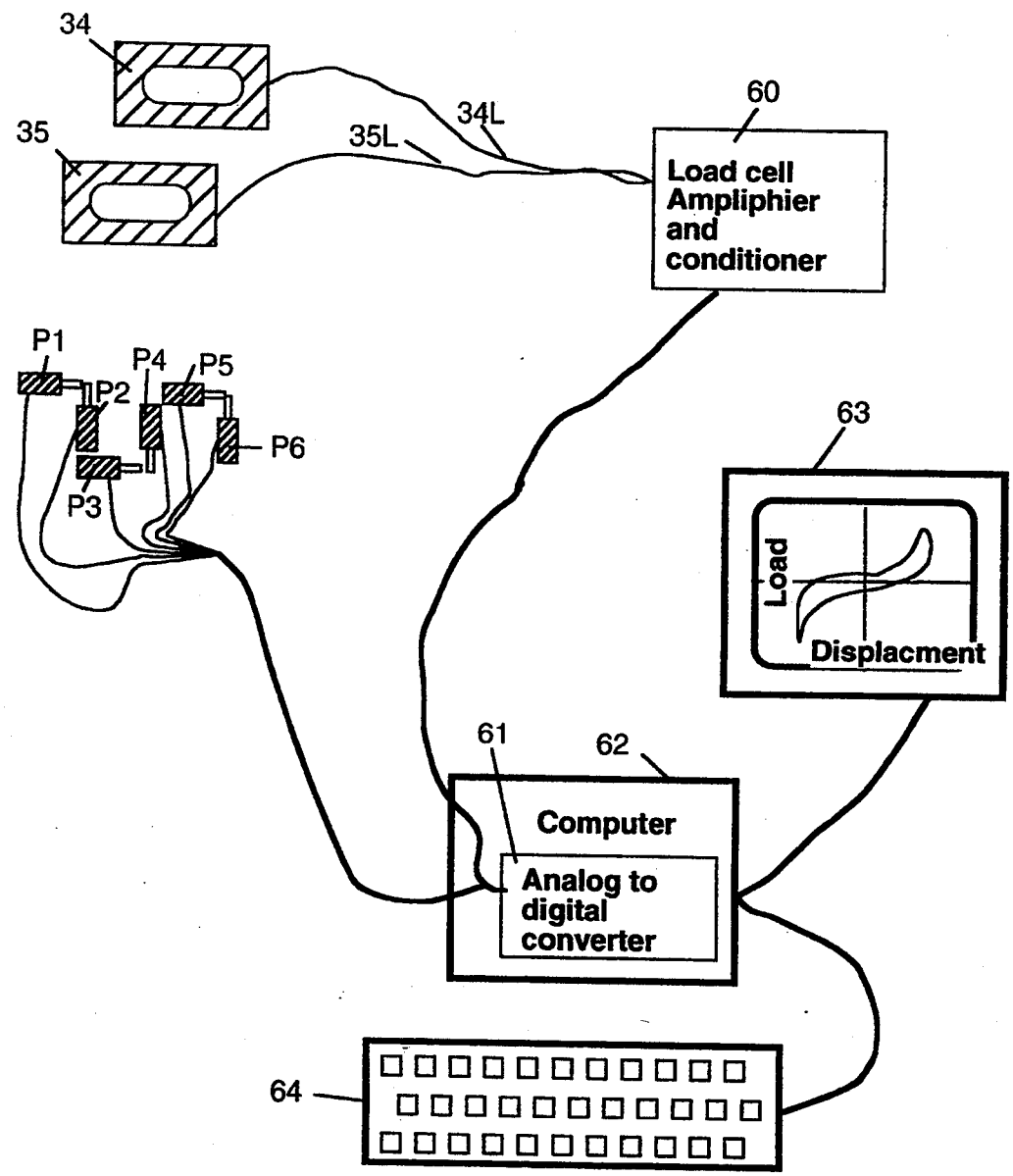
FIG. 7 is a schematic block diagram of the embodiment of the invention shown in FIG. 1.

Referring to FIG. 7, the anterior-posterior load cell 34 and the inversion-eversion torque load cells 35 are connected by leads 34L and 35L to a load cell amplifier and conditioner 60 which supplies these signals to an analog-to-digital converter 61 and thence to computer 62. In like manner, the signals from the six potentiometers P1, P2, P3, P4, P5 and P6 are coupled by a cabling 61 to the computer and these signals are likewise converted to analog-to-digital and supplied to the computer 62. The computer may be connected to a display 63 and a keyboard 64.

Figure 8:
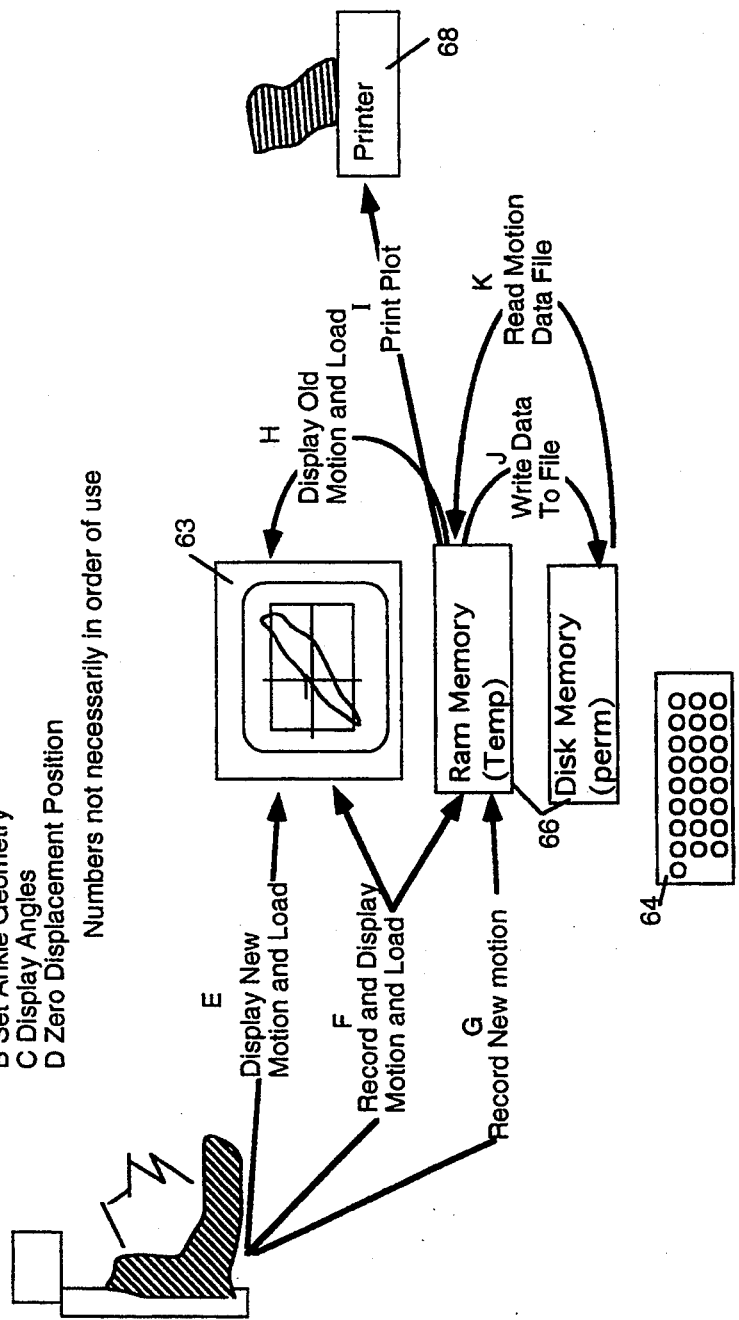
FIG. 8 is a schematic diagram showing the computer program routines and processes of the invention.

As shown in FIG. 8, the computer program routines include conventional routines for zeroing the load cells, setting-up the ankle geometry, the display angles and the zero displacement position. As shown in FIG. 8, the motion may be displayed on a display screen 63 and stored in a memory 66. The information may be stored in these memories and displayed on the display as well as being outputted to a printer 68.

Figure 6:
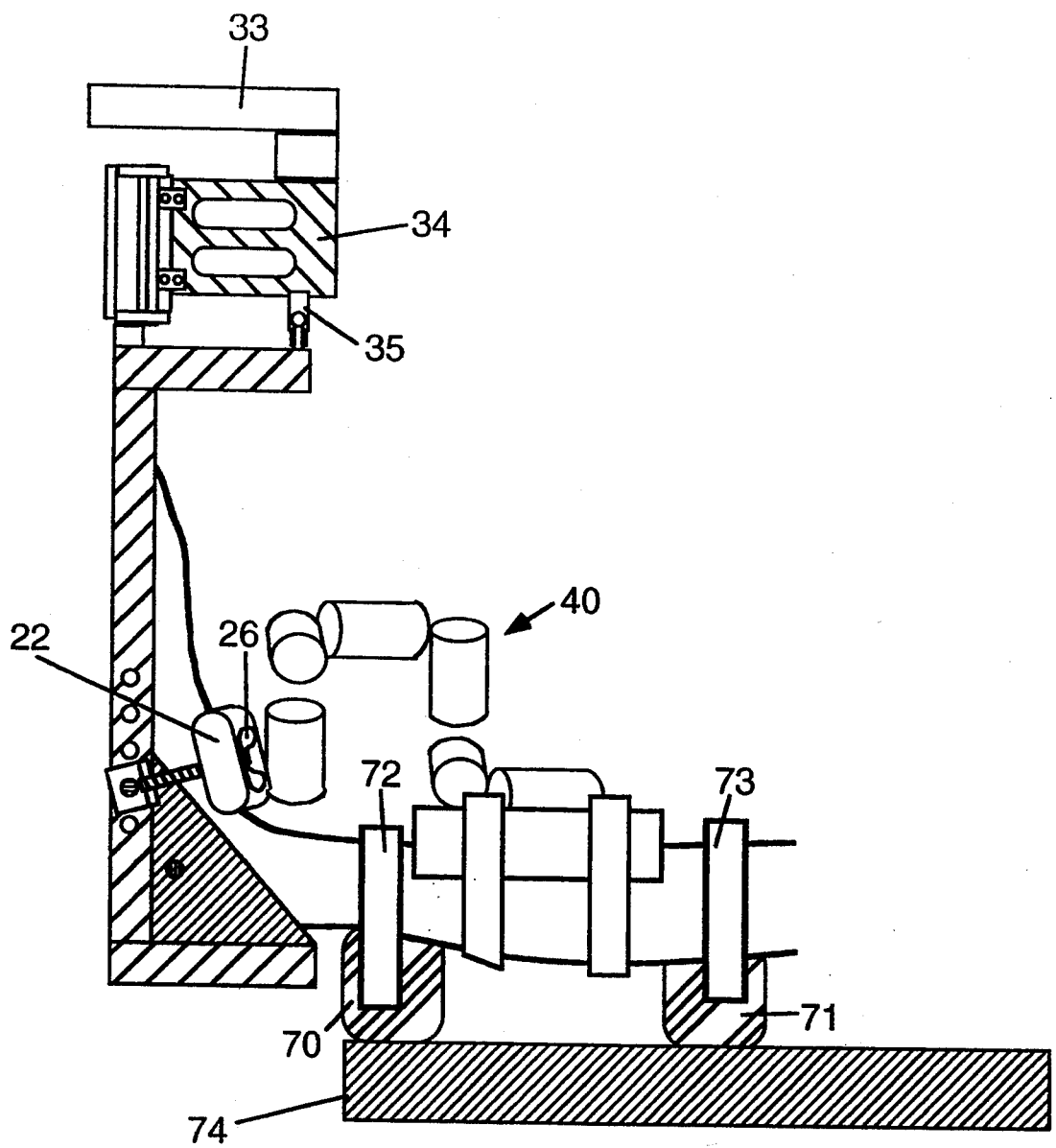
FIG. 6 is a side elevational view showing the invention being applied to a patient.

One manner of use of the apparatus of this invention is diagrammatically illustrated in FIG. 6 wherein leg support 70 and 71 have velcro straps 72, 73 which in effect immobilize the tibia on the end or edge of table 74. By grasping the load handle and applying a force, load cells 34, 35 measure the anterior-posterior loading and the inversion-eversion torque, respectively, which are supplied to computer 62 for processing and, in like manner, the outputs of rotary potentiometers P1...P6 are supplied to computer 62 for processing for display and recording in memory and/or outputting to a hard copy from printer 68.

Attachment of a foot clamp device to the foot requires first loosening the calcaneus pads and foot pad, placing the clamp on the foot and force anterior, tightening the foot clamp some and, then tightening the calcaneus pads slightly, tightening the foot pads securely and then tightening the calcaneus pads as much as is comfortable. A check should be made for slipping on the calcaneus or foot and the anterior-posterior or inversion-eversion directions and retightening if necessary. When testing, the foot clamps needs to be tight enough that the calcaneus does not separate or lose contact with the rear pad when applying an anterior-posterior force. The patient should be asked if they feel it is loose and if it is loose, the calcaneus must be forced against the posterior pad 20 (FIG. 2) and tighten the foot clamps so that it cannot separate from the posterior pad 20. Then the tibia clamp is applied to the tibia so as to make sure the linkage is in proper orientation. Place the tibia pad 42 on the tibia and tighten the tibia straps 43 checking the tibia pad 42 for looseness in tibial axial rotation, proximal distal translation and then retighten the straps, if necessary. Then the unit is zeroed to make sure that the six degrees of linkage and the anterior-posterior and inversion-eversion load cells 34 and 35, respectively, are zero. Then with the unit in ready state, the ankle is loaded and the anterior-posterior direction using load handle 33 which can be repeated if the curve is not satisfactory. This data then can be written to the disk file and printed on printer 68. The output of potentiometers P1...P6 provides a record of a particular movement of the ankle joint in the two planes of movement thereof whenever the anterior-posterior and inversion-eversion loading is applied to the ankle.

Figure 5:
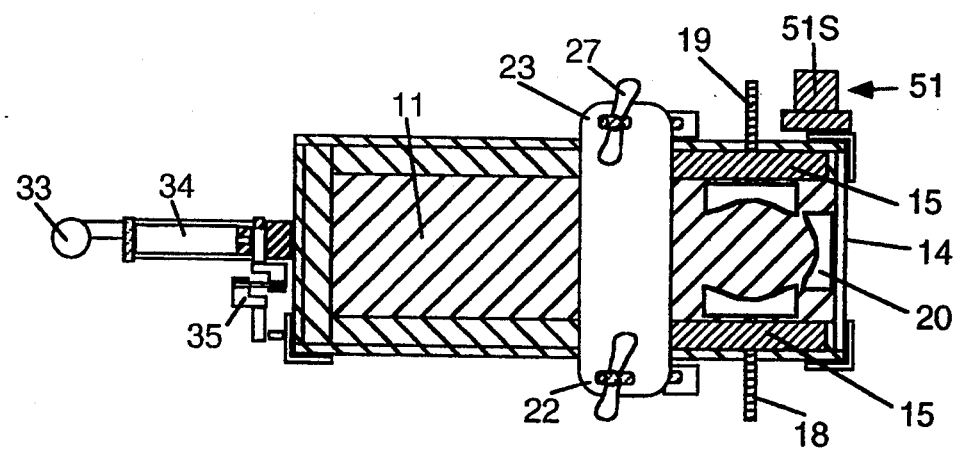
FIG. 5 is a top plan view of the embodiment shown in FIG. 4.
Figure 4:
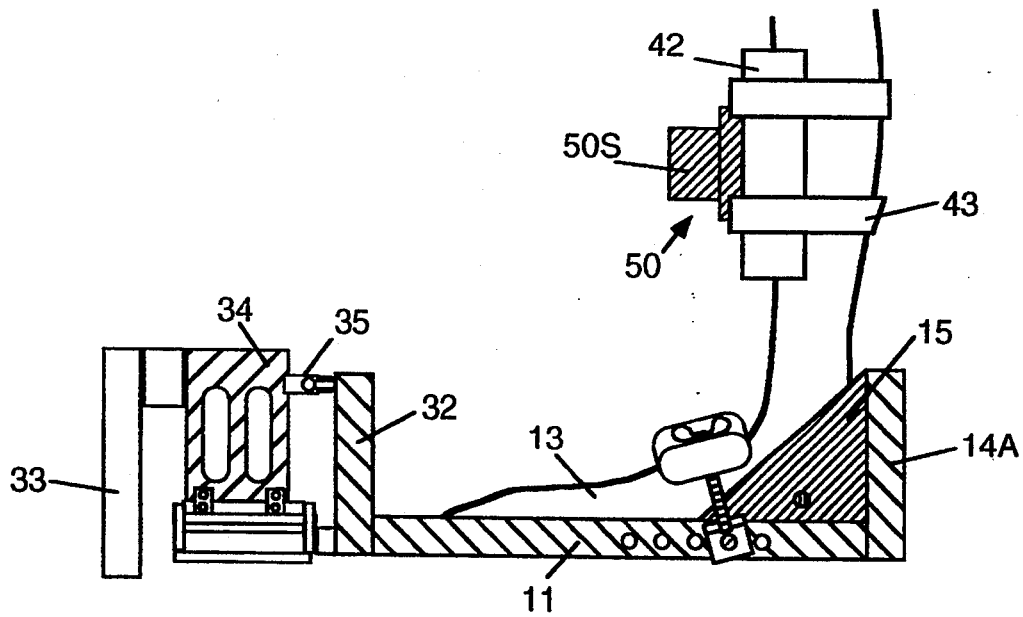
FIG. 4 is a side elevational view of a further embodiment of the invention.

In the embodiment shown in FIGS. 4 and 5, the spatial kinematic linkage 40 has been replaced by a different motion transducer system that achieves essentially the same six degree of freedom motion measurement. In this case, the six degree freedom of tracking is achieved by an electronic transducer system. One example of an electronic six degree of freedom transducer is manufactured by Polhemus Company under the trademark "3 SPACE FASTRAK ®". In this system, a transmitter 50 constituted by a small triad of electromagnetic coils enclosed in a plastic shell 50S that emits the electromagnetic fields. The transmitter is the system's reference frame for receiver measurements and is secured at the point of reference on the tibia in the same manner as the tibia end of the kinematic linkage 40. The receiver 51 is a small triad of electromagnetic coils enclosed in a further plastic shell 51S that detects the magnetic fields emitted by the transmitter. A systems electronic unit may be separate or provided in computer 62 and provides the signals to generate the magnetic fields, compute position, and orientation, and interface with other conventional components in computer 62. As the receiver is moved, its position and orientation is precisely measured as it is moved through space.

The remaining components shown in FIGS. 4 and 5 correspond to those described earlier herein in connection with FIGS. 1 and 2.

Figure 10:
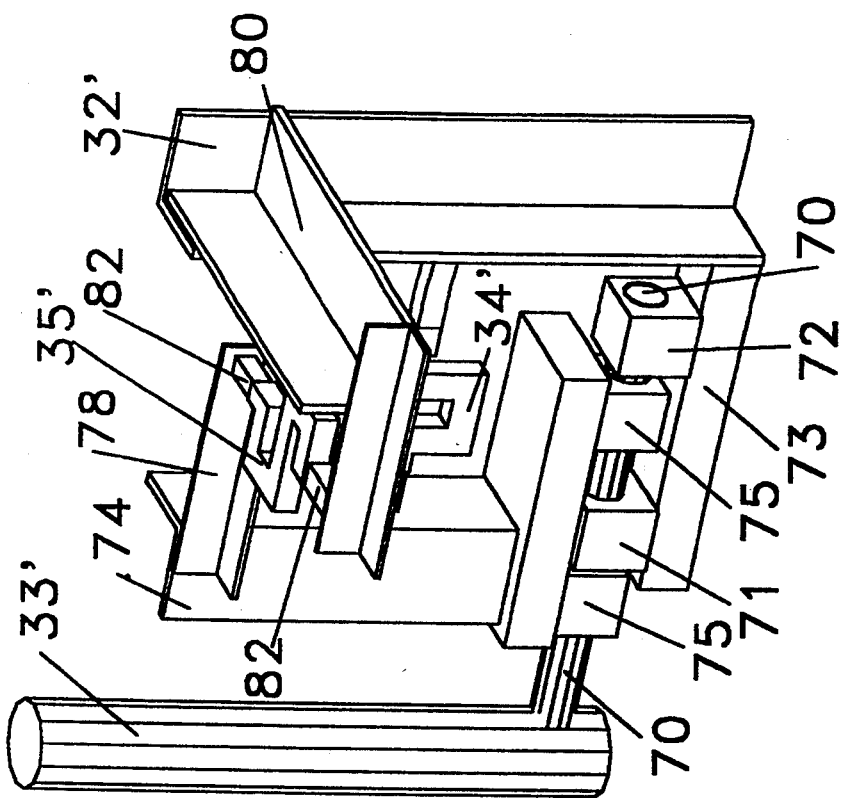
FIGS. 9 and 10 are perspective views showing a preferred construction for the anterior-posterior and inversion-eversion load cells and their connection to load handle, FIG. 10 being at a slightly different perspective angle.
Figure 9:
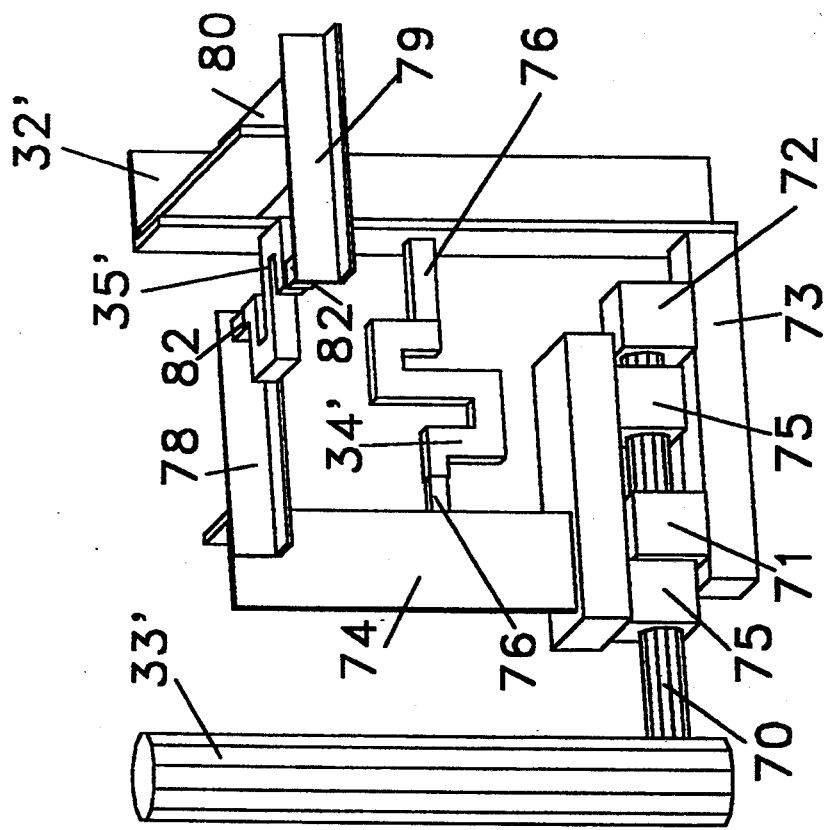

The perspective views of FIGS. 9 and 10 show load handle 33 secured to shaft 70 having a longitudinal axis and rotatably and translationally mounted in bearing journal blocks 71 and 72, which are mounted on extension plate 73 of the foot clamp frame member 11 (FIGS. 1, 2). Thus, shaft 70 is translatable or slidable along the longitudinal axis thereof and is rotatable along the longitudinal axis and fixed against all other motions relative to the foot frame. Lever arm 74 is secured to shaft 70 by mounting members 75 and transmits the axial shaft movements via ball joint 76, axially to anterior-posterior load cell 34', which is of the Omega #LCL-040-type on this embodiment. The opposite end of load cell 34' is coupled by a ball joint coupler 76 to the vertical member 32' at the toe end of foot clamp frame 11. Thus, axial forces transmitted through load cell 34' are measured and are an accurate measure of the anterior-posterior forces applied to the ankle joint and transmitted to AD61 and computer 62.

Lever arm 74 has an angle bracket member 78 secured thereof, preferably at the upper end as shown, and opposite a corresponding angle bracket 79, which is mounted from vertical member 32' by angle member 80. Inversion-eversion load cell 35' is mounted by ball joints 82. Thus, inversion-eversion forces are transmitted to foot clamp frame member 11 via load cell 35' and accurately measured thereby and transmitted to AD 61 and computer 62.

While I have shown and described preferred embodiments of the invention, it will be appreciated that other embodiments, modifications and adaptations of the invention will become readily apparent to those skilled in the art.

What is claimed is:

1. An ankle laxity measurement system for measuring laxity of the ankle and subtalar joint of a patient, comprising:
    a foot clamp frame,
    means for securing said foot clamp frame to said patient's foot,
    means for establishing a reference point on the patient's tibia above the patient's ankle,
    means for securing said means for establishing a reference point to the tibia of the patient,
    means to measure the motion between said foot clamp frame and said reference point in six degrees of freedom,
    handle means secured to said frame,
    force measuring means for measuring the force applied through said handle to said foot clamp frame, and
    means electrically connected to said means to measure and said force measuring means for recording and displaying the measured motion and forces.

2. The ankle laxity measurement system defined in claim 1 wherein said means for securing said foot clamp frame to said patient's foot comprises:
    pad means positioned on said foot clamp frame on either side of the calcaneus,
    pad means on the posterior of the calcaneus,
    a further pad means bridging the top of the patient's foot, means to adjust each said pad means to produce a secure fit on said patient's foot, and
    a plate positioned underneath said patient's foot.

3. The ankle laxity measurement system defined in claim 1 wherein said means for adjusting includes a series of selectable holes in said plate.

4. The ankle laxity measurement system defined in claim 1 wherein said means to measure the motion between said foot clamp frame and point of reference is comprised of a kinematic linkage between said point of reference and said foot clamp frame.

5. The ankle laxity measurement system defined in claim 4 wherein said kinematic linkage includes,
    six rotary potentiometers,
    bracket means of connecting said rotary potentiometers serially with each axes at a right angle to the previous rotary potentiometer in the chain.

6. The ankle laxity measurement system defined in claim 5 further including,
    an analog-to-digital converter,
    a computer system laving a computer program for sampling the angles of said potentiometers, and calculating the relative position of the two ends of said kinematic linkage.

7. The ankle laxity system defined in claim 1 wherein said means to measure motion includes a transmitter constituted by a first triad of coils secured to said point of reference and a receiver triad of coils secured to said foot clamp frame.

8. The ankle laxity measurement system defined in claim 7 further including,
    a digital-to-analog converter,
    a computer system for sampling the angles measured between said transmitter and said receiver, and
    calculating the relative positions between said transmitter and receiver.

9. The ankle laxity measurement system defined in claim 1 wherein said means to measure force includes load cells for measuring the anterior-posterior force and inversion-eversion torque applied to the foot.

10. The ankle laxity measurement system defined in claim 1 wherein said means to measure the force applied through said handle to the foot clamp frame, comprises:
    a shaft having a longitudinal axis,
    a handle secured to said shaft,
    a support means for said shaft allowing it to rotate around said long axis, slide along its long axis and fixed against all other motions,
    a first load cell mounted between said handle and said shaft support directed axially,
    connections for the load cell allowing it to pivot freely at both ends,
    a lever arm connected to the load handle,
    a second load cell connected between the lever arm and said shaft support and directed perpendicular to the handle shaft and handle lever arm,
    means supplying power to the load cells and means for amplifying the signals from said load cells and supplying same to said means to record and display.

11. The ankle laxity measurement system defined in claim 1 wherein said means for recording and displaying the measured motion and force includes:
an analog-to-digital converter,
computer with display, a software computer program installed in said computer for sampling the measurements, calculating the motion and displaying a curve of force vs. displacements.

12. A method for measuring the anterior-posterior and inversion-eversion laxity of a patient's ankle, comprising: the steps of:

1) providing a foot clamp frame having an anterior-posterior load measuring cell and an inversion-eversion load measuring cell and means for applying a force and torque to said foot clamp frame,
2) snugly securing directly the bare foot of the patient in said foot clamp frame,
3) establishing a point of reference on the patient's tibia above the patient's ankle, and immobilizing the patient's tibia,
4) applying a force and torque to said foot clamp frame and measuring the anterior-posterior and inversion-eversion forces applied to said frame, and
5) measuring the motion between said frame and said point of reference.

* * * * *